US008232393B2

(12) United States Patent
Adler et al.

(10) Patent No.: US 8,232,393 B2
(45) Date of Patent: Jul. 31, 2012

(54) AROMATIC AZA HETEROCYCLES, METHOD OF PRODUCTION AND USE OF THE MATERIAL IN ORGANIC ELECTRONICS

(75) Inventors: Jürgen Adler, Röttenbach (DE); Andreas Kanitz, Höchstadt (DE)

(73) Assignee: OSRAM Opto Semiconductors GmbH, Regensburg (DE)

( * ) Notice: Subject to any disclaimer, the term of this patent is extended or adjusted under 35 U.S.C. 154(b) by 123 days.

(21) Appl. No.: 12/373,504

(22) PCT Filed: Jul. 3, 2007

(86) PCT No.: PCT/EP2007/056688
§ 371 (c)(1),
(2), (4) Date: Aug. 12, 2009

(87) PCT Pub. No.: WO2008/006738
PCT Pub. Date: Jan. 17, 2008

(65) Prior Publication Data
US 2009/0318691 A1  Dec. 24, 2009

(30) Foreign Application Priority Data

Jul. 11, 2006  (DE) .......................... 10 2006 032 107

(51) Int. Cl.
*C07D 487/04* (2006.01)
*C07D 253/10* (2006.01)
*H01L 31/00* (2006.01)

(52) U.S. Cl. .................. 544/183; 548/302.1; 548/359.5; 428/690; 428/917; 313/504

(58) Field of Classification Search .................. 544/183; 548/302.1, 359.5; 428/690, 917; 313/504
See application file for complete search history.

(56) References Cited

U.S. PATENT DOCUMENTS 3,061,432 A   10/1962   Karl-Heinz et al.
2003/0104294 A1   6/2003   Law et al.

FOREIGN PATENT DOCUMENTS

EP    1 293 837    9/2002

*Primary Examiner* — Venkataraman Balasubramanian
(74) *Attorney, Agent, or Firm* — Cozen O'Connor

(57) ABSTRACT

An electron transport material based on fused aromatic electron-deficient compounds. The accumulation of aromatic rings with an electron deficiency allows free-radical anions to be stabilized very efficiently in these systems.

14 Claims, No Drawings

AROMATIC AZA HETEROCYCLES, METHOD OF PRODUCTION AND USE OF THE MATERIAL IN ORGANIC ELECTRONICS

RELATED APPLICATIONS

This is a U.S. national stage under 35 USC §371 of application No. PCT/EP2007/056688, filed on Jul. 3, 2007.

This application claims the priority of German Patent Application. 10 2006 032 107.3 filed Jul. 11, 2006, the disclosure content of which is hereby incorporated by reference.

FIELD OF THE INVENTION

The invention relates to a novel electron transport material based on fused aromatic electron-deficient compounds.

BACKGROUND OF THE INVENTION

Organic semiconductor materials are divided into hole and electron transport materials. These are required, for example, for the manufacture of so-called organic electronic components, such as organic light-emitting diodes (OLEDs), organic field-effect transistors (OFETs), organic solar cells, generally organic photo-voltaic elements, electrochromatic organic components, organic magnetic sensors, organic memory elements and/or organic photodetectors.

In the case of the hole transport materials, very efficient and stable structures have been developed in the last 15 years, which, according to the application, are available with a wide variety of different hole injection properties and form stable free-radical cations in the hole-transporting, oxidized state.

In the case of the electron transport materials, there are to date only very few representatives of this material property, both in terms of the range of electron injection and in terms of the stability of these materials in the electron-transporting, reducing state, and so, more particularly, the free-radical anions cannot be formed reversibly over a prolonged period.

Good electron conductors are considered at the present time to be the derivatives of phenanthroline (BCP and BPhen) and derivatives of oxadiazole. The free-radical anionic species which are formed during the operation of these components lead to a change in geometry in the heterocyclic structures, such that the electron trans-port propensity decreases as a consequence of the formation of interrupted conjugation.

SUMMARY OF THE INVENTION

One object of this invention is to provide more efficient electron conductors which are notable for a greater range of injection and in particular for the ability to form reversible free-radical anions of high stability.

One aspect of the present invention is directed to a heteroaromatic components comprising one of the following heterocyclic parent structures: a 1,2,4-benzotriazine A and/or B and/or pyrazolo-[1,5-a]-benzimidazole C and/or D,

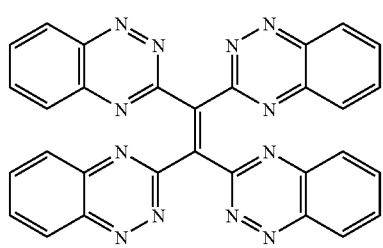

A

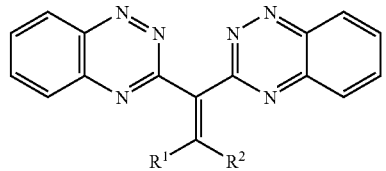

B

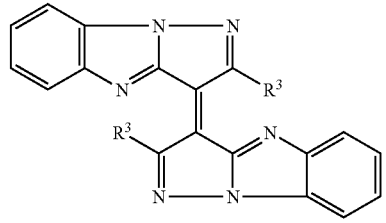

C

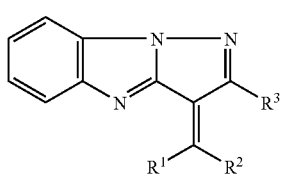

D in which the substituents $R^1$ and $R^2$ may each be defined independently as phenyl, 1-naphthyl, 2-naphthyl and/or any π-deficient aromatics. More particularly, π-deficient aromatics are understood to mean fused and unfused aromatic six-membered aza heterocyclic rings with one or more nitrogen atoms.

R3 is defined as aryl, especially phenyl, and alkyl, especially methyl.

Another aspect of the present invention is directed to the preparation of these components by reductive cyclization of nitroaromatics, and these components can be used in organic electronic components, as enumerated by way of example above.

DETAILED DESCRIPTION OF THE PREFERRED EMBODIMENTS

π-Deficient aromatics are considered to be all aromatic compounds in which the electron density in the aromatic ring is lowered with respect to the benzene ring.

They are formed either through substitution of a carbon atom for a more electronegative atom (e.g. nitrogen, sulfur, oxygen) given appropriate geometry of the system and/or for corresponding electronegative substitution of a hydrogen atom on a carbon of the base skeleton, which lowers the electron density in the aromatic ring to the effect that the aromatic ring has a high affinity for a further electron. More particularly, π-deficient aromatics are understood to mean fused and unfused aromatic six-membered aza heterocyclic rings with one or more nitrogen atoms. However, there are also five-membered π-deficient aromatic rings having at least 3 heteroatoms, more particularly S, O and N, which can be used, for example, instead.

Although there have already been many attempts to provide systems for stabilizing free-radical anions, which has been enabled particularly through introduction of Lewis-acidic derivatives, these systems, which are basically obtainable only via the method of reductive cyclization of nitroaromatics, have remained unexplored to date.

Since conjugated arrangements with extremely highly πelectron-deficient aromatics have been formed in these materials, they are also capable of stabilizing an additional electron in the π-system. This possibility of arranging different π-deficient heterocycles in the structure types B and D allows the range of injection to be varied significantly.

An illustrative synthesis scheme for preparation of the compounds is explained in detail hereinafter:

a) synthesis of the bis(1,2,4-benzotriazin-3-yl)-methane system: (reductive cyclization)

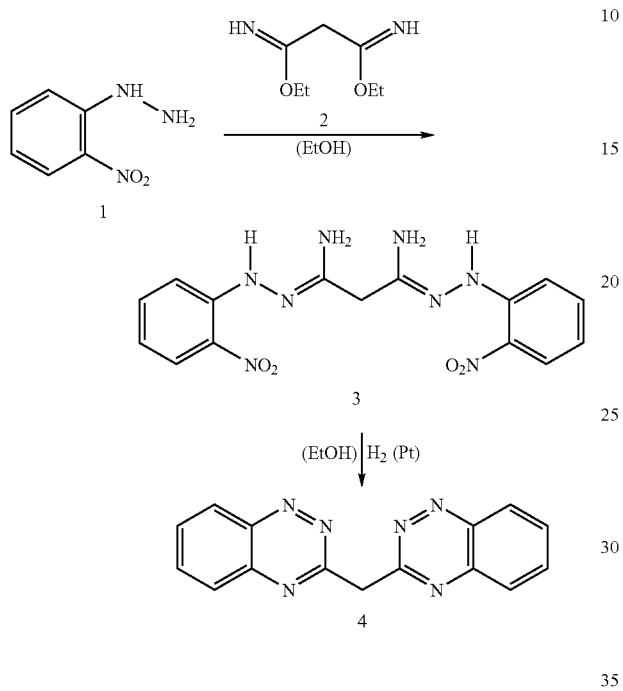

b) synthesis of 3-substituted pyrazolo-[1,5-a]-benzimidazoles:
(reductive cyclization)

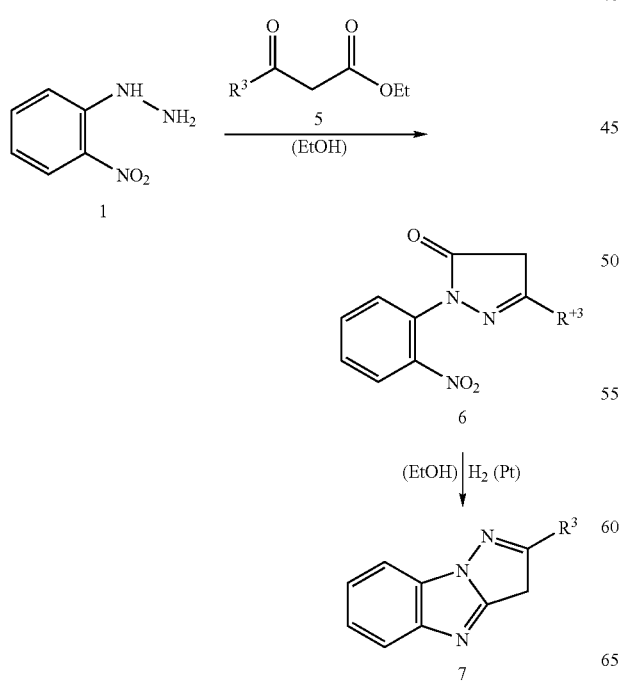

c) synthesis of tetra(1,2,4-benzotriazin-3-yl)-ethylene A:

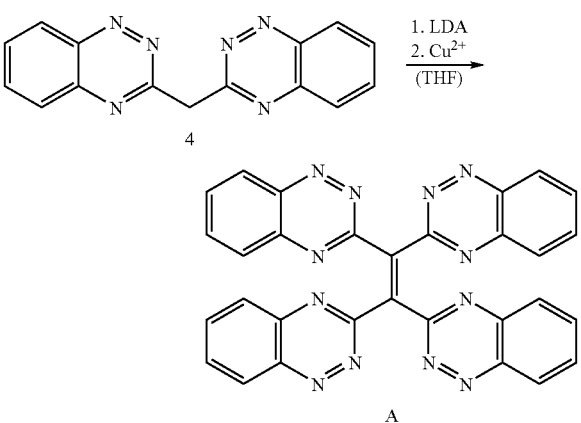

d) synthesis of 3,3'-substituted 4,4'-bis(pyrazolyleno-[1,5-a]-benzimidazoles) C:

e) synthesis of 1,1-diaryl-2,2-di(1,2,4-benzotriazin-3-yl) ethylenes B:

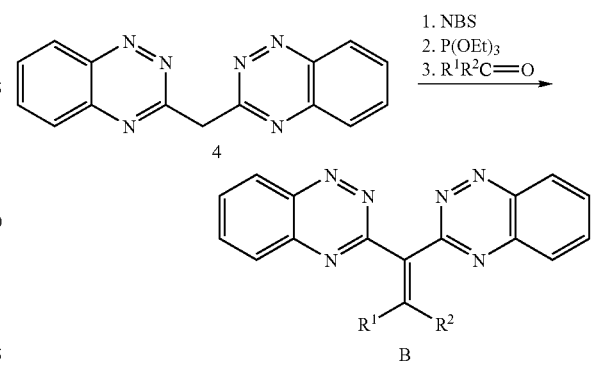

f) synthesis of 4-diarylmethylene-substituted pyrazolo-[1,5-a]-benzimidazoles D:

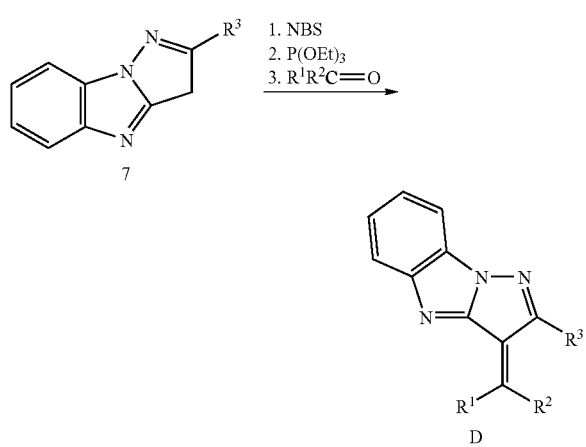

WORKING EXAMPLES a) Synthesis of the bisamidrazone 3

0.1 mol of o-nitrophenyl hydrazine 1 and 0.05 mol of diethyl diiminomalonate 2 are heated at reflux in 200 ml of ethanol for 4 h. After cooling, the crystallized bisamidrazone 3 is filtered off with suction, m.p.=° C., yield 70% of theory.

b) Synthesis of bis(1,2,4-benzotriazin-3-yl)methane 4

A hydrogenation apparatus is initially charged with 5 g of the bisamidrazone 3 in 200 ml of ethanol, admixed with a spatula-tip of $PtO_2$ and then hydrogenated under a hydrogen atmosphere at room temperature until no further hydrogen is taken up. The resulting yellow solution is separated from the platinum catalyst with exclusion of air and heated at reflux under inert gas for 2 h until the elimination of the ammonia is complete. Thereafter, the solution is oxidized with atmospheric oxygen for 2 h. The solution is concentrated on a rotary evaporator and crystallized.

c) Synthesis of the 1-(o-nitrophenyl)pyrazolones 6

0.1 mol of o-nitrophenyl hydrazine 1 and 0.12 mol of a β-keto ester 4 are heated at reflux in 200 ml of ethanol for 2 h. After cooling, the mixture is concentrated by ⅔ on the rotary evaporator and the pyrazolone 6 is crystallized, m.p.=° C., yield 65% of theory.

d) Synthesis of the pyrazolo-[1,5-a]-benzimidazoles 7

A hydrogenation apparatus is initially charged with 5 g of the pyrazolone 6 into 200 ml of ethanol, admixed with a spatula-tip of $PtO_2$ and then hydrogenated under a hydrogen atmosphere at room temperature until no further hydrogen is taken up. The resulting colorless solution is separated from the platinum catalyst with exclusion of air and then heated at reflux until complete condensation of 7 for 1 h. The solution is concentrated on a rotary evaporator and crystallized. The product is a colorless amorphous powder, m.p.=° C., yield 55% of theory.

e) Synthesis of tetra(1,2,4-benzotriazin-3-yl)-ethylene A 2 g of bis(1,2,4-benzotriazin-3-yl)methane 4 are dissolved in 100 ml of dry THF in an inert apparatus and admixed with twice the equivalent amount of LDA. The dark-colored solution is then admixed with dry copper(II) chloride. After heating for 30 min, the mixture is concentrated on a rotary evaporator, admixed with water and dilute hydrochloric acid and finally extracted by shaking with chloroform. The chloroform phase is concentrated after drying, and the product A is precipitated with ethanol and ether.

f) Synthesis of 3,3'-substituted 4,4'-bis(pyrazolyleno-[1,5-a]-benzimidazoles) C 2 g of pyrazolo-[1,5-a]-benzimidazole 7 are dissolved in 100 ml of dry THF in an inert apparatus and admixed with twice the equivalent amount of LDA. The dark-colored solution is then admixed with dry copper(II) chloride. After heating for 30 min, the mixture is concentrated on a rotary evaporator, admixed with water and dilute hydrochloric acid and finally extracted by shaking with chloroform. The chloroform phase is concentrated after drying, and the product C is precipitated with ethanol and ether.

g) Synthesis of 1,1-diaryl-2,2-di(1,2,4-benzotriazin-3-yl)ethylenes B 0.01 mol of bis(1,2,4-benzotriazin-3-yl)methane 4 is dissolved in 50 ml of Tetra and admixed with the equivalent amount of NBS. After the solution has been heated at reflux for 6 h, the mixture is filtered with suction at approx. 40° C. and the filtrate is concentrated to dryness. The residue is admixed with the equivalent amount of triethyl phosphite, 50 ml of toluene and 1.5 equivalents of the desired diaryl ketone. Thereafter, the reaction mixture is heated at approx. 100° C. in an oil bath and 2 equivalents of potassium tert-butoxide are added to the solution after the oil bath temperature has been attained. After a further 2 h, the mixture is worked up by freeing it of the solvent on a rotary evaporator, and the product B is extracted by adding water, dilute hydrochloric acid and chloroform. After the chloroform phase has been dried, the mixture is again concentrated and the crude product is precipitated from a mixture of ethanol and ether.

h) Synthesis of 4-diarylmethylene-substituted pyrazolo-[1,5-a]benzimidazoles D 0.01 mol of pyrazolo-[1,5-a]-benzimidazole 7 is dissolved in 50 ml of Tetra and admixed with the equivalent amount of NBS. After heating the solution at reflux for 6 h, the mixture is filtered with suction at approx. 40° C. and the filtrate is concentrated to dryness. The residue is admixed with the equivalent amount of triethyl phosphite, 50 ml of toluene and 1.5 equivalents of the desired diaryl ketone. Thereafter, the reaction mixture is heated at approx. 100° C. in an oil bath and 2 equivalents of potassium tert-butoxide are added to the solution after the oil bath temperature has been attained. After a further 2 h, the mixture is worked up by freeing it of the solvent on a rotary evaporator, and the product D is extracted by adding water, dilute hydrochloric acid and chloroform. After the chloroform phase has been dried, the mixture is again concentrated and the crude product is precipitated from a mixture of ethanol and ether.

The high free-radical ion stability of the compounds according to the invention achieves the effect that the materials produced therefrom can be used very efficiently as electron conductors for organic electronic components. The substances are soluble in common solvents and can be introduced into printable pastes or dispersions, such that they can be processed in a manner suitable for mass production.

One aspect of the invention relates to a novel electron transport material based on fused aromatic electron-deficient compounds. The accumulation of aromatic rings with an electron deficiency allows free-radical ions to be stabilized very efficiently in these systems.

The scope of protection of the invention is not limited to the examples given hereinabove.

The invention is embodied in each novel characteristic and each combination of characteristics, which includes every combination of any features which are stated in the claims, even if this feature or combination of features is not explicitly stated in the examples.

The invention claimed is:

1. A heteroaromatic compound having a chemical formula B, C, or D as shown below:

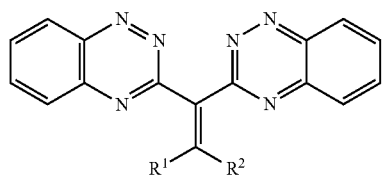

B

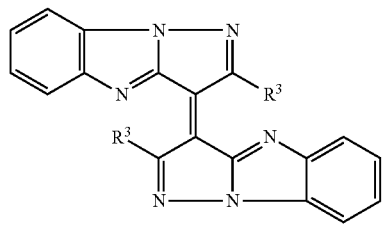

C

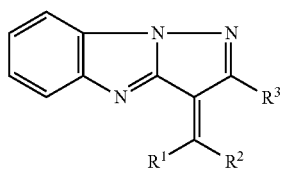

D wherein each of $R^1$ and $R^2$ is independently selected from the group consisting of phenyl, 1-naphthyl, 2-naphthyl, and a π-deficient aromatic compound; and
$R^3$ is aryl or alkyl.

2. The compound of claim 1 having a chemical formula C or D as shown in claim 1, wherein $R^3$ is phenyl.

3. The compound of claim 1 having a chemical formula C or D as shown in claim 1, wherein $R^3$ is methyl.

4. The compound of claim 1 having a chemical formula B or D as shown in claim 1, wherein the π-deficient aromatic compound is selected from fused and unfused aromatic six-membered aza heterocyclic compounds with one or more nitrogen atoms.

5. The compound of claim 1 having a chemical formula B or D as shown in claim 1, wherein the π-deficient aromatic compound is selected from five-membered π-deficient aromatic compounds having at least 3 heteroatoms.

6. The compound of claim 1 having a general chemical formula B as shown in claim 1 and a specific chemical formula A as shown below:

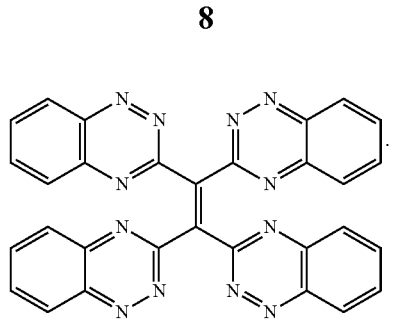

A

7. A process for preparing a heteroaromatic compound having a chemical formula B, C, or D as shown below:

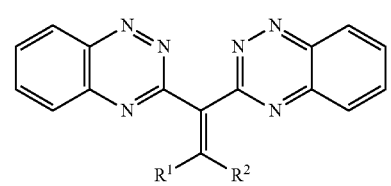

B

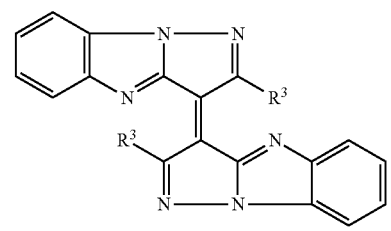

C

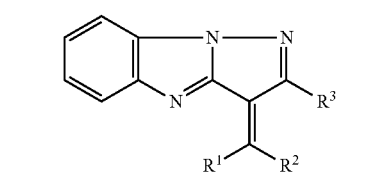

D wherein each of $R^1$ and $R^2$ is independently selected from the group consisting of phenyl, 1-naphthyl, 2-naphthyl, and a π-deficient aromatic compound; and
$R^3$ is aryl or alkyl, wherein a compound of formula 4

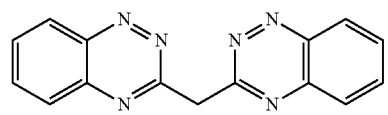

4 is converted to the compound of formula B; or a compound of formula 7

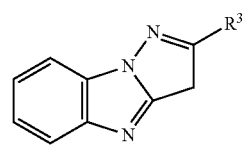

7 is converted to the compound of formula C or D;

wherein the step of converting the compound of formula 7 to the compound of formula D comprises reacting the compound of formula 7 with a compound of formula $R^1R^2C{=}O$.

8. The process of claim 7 wherein
the compound of formula 4 is prepared by a process comprising: 1) reacting a compound of formula 1

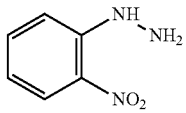
1 with a compound of formula 2

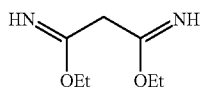
2 to form a compound of formula 3;

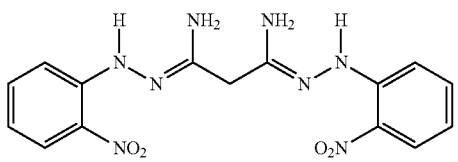
3 and 2) converting the compound of formula 3 to the compound of formula 4

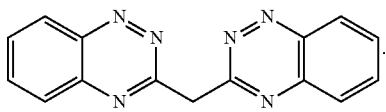
4

9. The process of claim 7 wherein the compound of formula 7 is prepared by a process comprising: 1) reacting a compound of formula 1

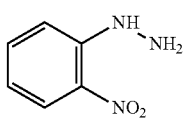
1 with a compound of formula 5

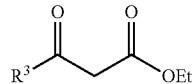
5 to form a compound of formula 6;

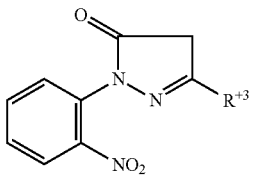
6 and 2) converting the compound of formula 6 to the compound of formula 7

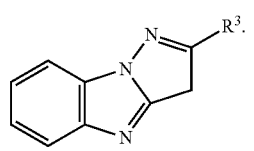
7

10. An electronic device comprising an electronic transport component, wherein the electronic transport component comprises a compound of claim 1.

11. The process of claim 7 wherein the step of converting the compound of formula 4 to the compound of formula B comprises dimerizing the compound of formula 4 or reacting the compound of formula 4 with a compound of formula $R^1R^2C{=}O$, wherein each of $R^1$ and $R^2$ is independently selected from the group consisting of phenyl, 1-naphthyl, 2-naphthyl, and a π-deficient aromatic compound.

12. The process of claim 7 wherein the step of converting the compound of formula 7 to the compound of formula C comprises dimerizing the compound of formula 7.

13. The process of claim 8 wherein the compound of formula 3 is converted to the compound of formula 4 via hydrogenation and cyclization.

14. The process of claim 9 wherein the compound of formula 6 is converted to the compound of formula 7 via hydrogenation and cyclization.

* * * * *